(12) United States Patent
Van Dongen et al.

(10) Patent No.: US 10,802,023 B2
(45) Date of Patent: Oct. 13, 2020

(54) REAGENTS, METHODS AND KITS FOR DIAGNOSING PRIMARY IMMUNODEFICIENCIES

(71) Applicant: Erasmus University Medical Center Rotterdam, Rotterdam (NL)

(72) Inventors: Jacobus Johannes Maria Van Dongen, Rotterdam (NL); José Alberto Orfao De Matos Correia E Vale, Salamanca (ES); Mirjam Van Der Burg, Rotterdam (NL); Martin Pérez-Andrés, Salamanca (ES); Menno Cornelis Van Zelm, Rotterdam (NL); Tomáš Kalina, Prague (CZ); Marcela Vlková, Brno (CZ); Eduardo López-Granados, Madrid (ES); Elena Blanco Álvarez, Salamanca (ES); Anne-Kathrin Kienzler, Oxford (GB)

(73) Assignee: ERASMUS UNIVERSITY MEDICAL CENTER ROTTERDAM, Rotterdam (NL)

( * ) Notice: Subject to any disclaimer, the term of this patent is extended or adjusted under 35 U.S.C. 154(b) by 301 days.

(21) Appl. No.: 15/523,309

(22) PCT Filed: Oct. 30, 2015

(86) PCT No.: PCT/NL2015/050762
§ 371 (c)(1),
(2) Date: Apr. 28, 2017

(87) PCT Pub. No.: WO2016/068714
PCT Pub. Date: May 6, 2016

(65) Prior Publication Data
US 2018/0017560 A1   Jan. 18, 2018

Related U.S. Application Data

(60) Provisional application No. 62/072,498, filed on Oct. 30, 2014.

(51) Int. Cl.
G01N 33/569 (2006.01)
G01N 15/14 (2006.01)
G01N 15/00 (2006.01)
G01N 15/10 (2006.01)

(52) U.S. Cl.
CPC ... G01N 33/56972 (2013.01); G01N 15/1459 (2013.01); G01N 2015/008 (2013.01); G01N 2015/1006 (2013.01); G01N 2015/1402 (2013.01); G01N 2015/1477 (2013.01); G01N 2015/1488 (2013.01); G01N 2800/24 (2013.01)

(58) Field of Classification Search
CPC ......... G01N 33/56972; G01N 15/1459; G01N 2015/008; G01N 2015/1006; G01N 2015/1402; G01N 2015/1477; G01N 2015/1488; G01N 2800/24
See application file for complete search history.

(56) References Cited

U.S. PATENT DOCUMENTS

| 7,321,843 B2 | 1/2008 | De Matos Correia E Valle et al. |
| 7,507,548 B2 | 3/2009 | De Matos Correia E Valle et al. |

FOREIGN PATENT DOCUMENTS

| EP | 2780711 A1 | 9/2014 |
| WO | WO2010140885 A1 | 12/2010 |

OTHER PUBLICATIONS

Warnatz et al. Immune phenotyping in primary immunodeficiency. IPID Protocols (2010).*
O'Gorman et al. Flow Cytometry Assays in Primary Immunodeficiency Disease. Methods in Molecular Biology 699: 317-335 (2011).*
Fridberg et al. Diffuse large B cell lymphoma—in vitro characterization and emphasis on PKC-beta and protein tyrosine phosphatase expression. Immunology 210 (6-8): 462-463 (2005).*
Boldt, et al. "Eight-color immunophenotyping of T-, B-, and NK-cell subpopulations for characterization of chronic immunodeficiencies," Cytometry Part B (Clinical Cytometry), Jan. 16, 2014, pp. 191-206, vol. 86, No. 3, Gemany.
Fridberg, et al., "Diffuse large B cell lymphoma—in vitro characterization with emphasis on PKC-beta and protein tyrosine phosphatase expression," Immunobiology, 2005, pp. 462-463, vol. 210, No. 6-8.
International Search Report issued in International Application No. PCT/NL2015/050762 dated May 27, 2016, 9 pages.
Kamphuis et al., "Perigranuloma Localization and Abnormal Maturation of B Cells," American Journal of Respiratory and Critical Care Medicine, Feb. 15, 2013, pp. 406-416, vol. 187, No. 4.
Locke, et al.,"Laboratory Diagnosis of Primary Immunodeficiencies," Clinical Reviews in Allergy and Immunology, Feb. 26, 2014, pp. 154-168, vol. 46, No. 3, New York.
Maecker, et al., "Standardizing immunophenotyping for the Human Immunology Project," Nature Reviews Immunology, Feb. 17, 2013, pp. 191-200, vol. 12, U.S.A.
O'Gorman, el al., "Flow Cytometry Assays in Primary Immunodeficiency Diseases," Methods in Molecular Biology, 2011, pp. 317-335, vol. 699.
Rakhmanov, et al., "Circulating CD21low B cells in common variable immunodeficiency resemble tissue homing, innate-like B cells," PNAS USA, 2009, pp. 13451-13456, vol. 106, No. 32.

(Continued)

Primary Examiner — Gailene Gabel
(74) Attorney, Agent, or Firm — Dentons US LLP

(57) ABSTRACT

This invention relates to the field of primary immunodeficiencies (PID), more specifically to means and method for the diagnosis of PID of the lymphoid system. Provided are unique reagent compositions for the flow cytometric immunophenotyping of leukocytes comprising fluorochrome-conjugated antibodies directed against various specific combinations of markers. Also provided are kits comprising the reagent compositions, and methods using the same.

7 Claims, 8 Drawing Sheets

(56) References Cited

OTHER PUBLICATIONS

Figure 1A:
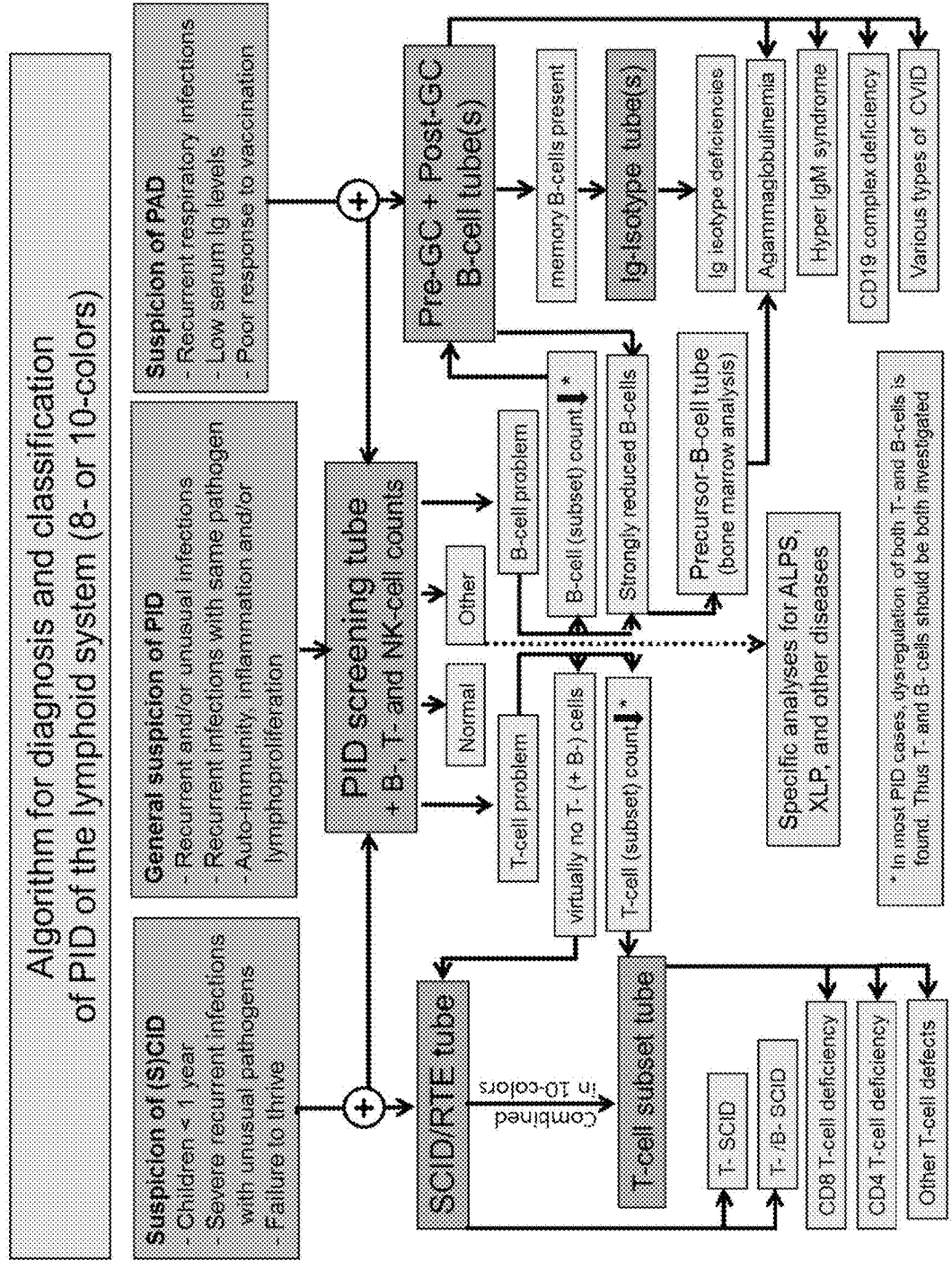

Warnatz, et al., "Immune phenotyping in primary immunodeficiency," 2010, retrieved from the internet at http://www.ipidnet.org/protocol-data-1, pp. 1-5.

Van Dongen J. J., et al., "EuroFlow antibody panels for standardized n-dimensional flow cytometric immunophenotyping of normal, reactive and malignant leukocytes," Leukemia, 2012, 26, 1908-1975.

Streitz M., et al., "Standardization of whole blood immune phenotype monitoring for clinical trials: panels and methods from the ONE study," Transplant Res, 2013, 2, 17.

Oliveira J. B., et al., "Applications of flow cytometry for the study of primary immune deficiencies," Curr Opin Allergy Clin Immunol, 2008, 8, 499-509.

O'Gorman MR, et al., "Flow cytometry assays in primary immunodeficiency diseases," Methods Mol. Biol., 2011, 699, 317-335.

Mishra A., et al., "Rapid Flow cytometric prenatal diagnosis of primary immunodeficiency (PID) disorders," J Clin Immunol, 2014, 34, 316-322.

Maecker H.T., "Standardizing immunophenotyping for the Human Immunology Project," Nature Reviews, 2012, 12, 191-200.

Kalina T., et al., "EuroFlow standardization of flow cytometer instrument settings and immunophenotyping protocols," Leukemia, 2012, 26, 1986-2010.

Duffy D, et al., "Functional analysis via standardized whole-blood stimulation systems defines the boundaries of a healthy immune response to complex stimuli," Immunity, 2014, 40, 436-50.

Boldt A., et al., "Eight-color immunophenotyping of T-, B-, and NK-cell subpopulations for characterization of chronic immunodeficiencies," Cytometry B Clin Cytom, 2014, 86, 191-206.

Biancotto A., et al., "High dimensional flow cytometry for comprehensive leukocyte immunophenotyping (CLIP) in research," J Immunol Meth, 2011, 363, 245-61.

Al-Herz W., et al., "Primary Immunodeficiency Diseases : An Update on the Classification from the International Union of Immunological Societies Expert Committee for Primary Immunodeficiency," Front Immunol, 2014, 5, 162.

Van Dongen J et al., "EuroFlow-Based Flowcytometric Diagnostic Screening and Classification of Primary Immunodeficiencies of the Lymphoid System Frontiers in Immunology," 2019, 10, Article 1271.

* cited by examiner

REAGENTS, METHODS AND KITS FOR DIAGNOSING PRIMARY IMMUNODEFICIENCIES

CROSS REFERENCE TO RELATED APPLICATIONS

This application is the U.S. National Stage of International Patent Application No. PCT/NL2015/050762, filed Oct. 30, 2015, published in English, which claims priority to International Patent Application No. PCT/NL2015/050762, filed Oct. 30, 2015, and priority to U.S. Provisional Application No. 62/072,498, filed Oct. 30, 2014.

This invention relates to the field of primary immunodeficiencies (PID), more specifically to means and method for the diagnosis of PID of the lymphoid system. PID are inherited disorders of the immune system. PID patients generally present with recurrent, severe and sometimes life-threatening infections. To date, more than 200 genes have been identified that can be mutated in PID patients (Al Herz, Front Immunol 2014; 5:162). Depending on the genetic defect, one part of the immune system or one cell type can be absent or dysfunctional. The majority of patients with a PID have a defect of the adaptive immune system, i.e. involving a defect in B- and/or T-cells. Flow cytometric immunophenotyping plays a crucial role in the stepwise diagnostic process of PID patients. Correct diagnosis is of utmost importance, because it determines the therapeutic strategy, which includes antibiotics, immunoglobulin substitution or, in some cases, hematopoietic stem cell transplantation or gene therapy.

Many diagnostic and research centers have developed multi-color flow cytometric protocols for diagnosis and classification of PID, but differences in antibody panels, sample handling, instrument setup and data analysis hamper reproducibility or exchange of data between centers. Especially for PID there is a need to exchange data between centers, because of large numbers of different PID, the low incidence of PID and the clinical and immunological heterogeneity of PID.

Several monoclonal antibody (MoAb) panels have been proposed for the flow cytometric analysis of PID of the lymphoid system. Most of these MoAb panels are devoted to the identification of major defects in B and T lymphocytes as well as NK-cells, and/or the diagnostic screening for a specific inherited disorder. Examples of such disease-specific oriented flow cytometric MoAb panels are: panels for the diagnostic screening and classification of severe combined immunodeficiency (SCID) based on the quantification of the B-, T- and NK-cells with CD3, CD19 and CD56 alone or in combination with CD16; the diagnostic screening of congenital agammaglobulinemia based on the enumeration of circulating (e.g. CD19+) B-lymphocytes; the classification of common variable immunodeficiency (CVID) according to the proportion of immature/transitional, non-switched/marginal zone-like (smIgMD$^+$) and class-switched (smIgMD$^-$), and CD21dim B-lymphocytes; diagnostic screening of DiGeorge syndrome patients based on the relative counts of recent thymic emigrant (RTE) CD4+ T-cells in peripheral blood, and; the quantification of CD4 and CD8-double negative TCRαβ$^+$ T-cells (DNT) for the screening of autoimmune lymphoproliferative syndrome (ALPS) (Oliveira et al, Curr Opin Allergy Clin Immunol 2008; 8: 499). Such MoAb panels are typically focused on the detection and enumeration of disease-associated lymphocyte subpopulations only. Consequently, none of these approaches allows for a complete overview and detailed description of the distribution of distinct subsets of circulating leukocytes.

In parallel, comprehensive immunophenotypic panels have been proposed and used for the study of multiple different subpopulations of peripheral blood leukocytes, such as the so-called EuroFlow antibody panels (see WO2010/140885 A1), the comprehensive leukocyte immunophenotyping panel (CLIP; Biancotto et al, J Immunol Meth 2011; 363:245), an antibody panel for harmonizing flow cytometry in clinical trials (Maecker et al, Nat Immunol 2012; 12: 191) the ONE study MoAb panel (Streitz et al, Transplant Res 2013; 2: 17), and the Pasteur Immunophenotyping panel (Duffy et al, Immunity 2014; 40:436). These known panels allow for the identification of several subpopulations of B-, T- and NK-cells (e.g. naive vs. memory, activated cells, TCRγδ vs. TCRαβ) together with the identification of monocytes, dendritic cells, and granulocytes. However, the combinations proposed in these MoAb panels specifically focus on the identification and enumeration of leukemia/lymphoma cell populations or monitoring of specific T, B and NK cell compartments using multiple MoAb tubes that only provide information relevant for specific conditions, such as immune monitoring after transplantation, but not in other conditions such as PID.

More recently, a specific MoAb panel has been proposed for the analysis of lymphocyte subpopulations in peripheral blood which aims at the diagnosis of PID patients. This panel is claimed to comprise a "general lymphocyte overview" MoAb combination for the identification of total T-, B- and NK-cells, together with seven additional MoAb combinations for the immunophenotypic characterization of these cells with markers which have proven to be clinically relevant for the diagnosis and classification of PID patients (Bolt et al. Cytometry B Clin Cytometry 2014; 86: 191; O'Gorman et al. Methods Mol Biol 2011; 699: 317). Most of these MoAb combinations (six out of seven) are directed to T- and NK-cells allowing an extensive description of these subsets including discrimination of functional subsets (e.g. helper vs. cytotoxic), maturation stage (e.g. naive, memory, effector and effector memory), and other disease-associated subpopulations (e.g. RTE and DNT cells). In contrast, a more limited dissection of the B-cell compartment is attained as its remains restricted to the delineation of the maturation stage-associated cell compartments of immature/transitional, naive, non-switched and class-switched memory B-cells, and plasmablasts/plasma cells; further dissection of these B-cell subsets into other compartments which are specifically involved in PID, such as Ig isotype subsets, cannot be obtained with this approach. In fact, although quantification of the serum immunoglobulin levels of the different isotypes is mandatory in most of the PID patients, none of the published methods is able to identify the cellular counterpart of these immunoglobulins (IgM, IgD, IgG1, IgG2, IgG3, IgG4, IgA1, and IgA2) in the B-cell compartment in maximally two tubes. In addition, the proposed panel does not provide information about other subsets of circulating leukocytes such as: dendritic cells, basophils or eosinophils, among other cells.

Another limitations for this method is that only two examples of the application on PID patients have been provided, both from the same center, and no information is available about the performance of the method in a representative series of PID patients in a multicenter setting. Finally, the relatively high number of tubes which are required to be stained in patients (e.g. frequently children) with extremely low T-cell counts, leads to the need for high sample volumes or arbitrary decisions about which subset of tubes can be stained in a specific patient, due to limited sample availability.

In summary, current MoAb protocols and techniques for the flow cytometric diagnosis of PID have several major limitations. These protocols have not been designed for stepwise screening and classification of PID patients. Instead, they are typically focused on a single and relatively uniform disease subgroup, they do not provide information on how to combine the recommended MoAb markers with specific fluorochromes, they only permit simultaneous assessment of a fraction of all relevant cell subsets (without full description of the distinct immune cell compartments), and they do not classify B-cells according to the produced immunoglobulin isotype(s). Finally, these protocols have been evaluated in very limited numbers of PID samples and/or they have not been proven to be sufficiently standardized to work in a multicenter setting.

The present inventors therefore aimed at the provision of means and methods for the unequivocal identification and full dissection of both maturation and functional subsets of lymphocytes, together with other leukocyte subpopulations which show distinct patterns of alteration in distinct PID patients. To that end, appropriate combinations of well-defined antibodies in multicolor tubes were designed and evaluated and optimized in multiple multicenter testing rounds. In addition, specific combinations of fluorochromes bound to the antibody reagents were selected based on the need for brightness, compensation, stability, etc., to develop a set of antibody reagents that could be applied stepwise for the diagnosis and classification of PID (see stepwise diagnostic algorithm in FIG. 1).

The proposed MoAb panels of the invention were extensively evaluated in multicenter studies by analyzing both healthy control samples and samples of PID patients from different diagnostic groups, such as SCID, CVID, DiGeorge syndrome, ALPS, Wiskott Aldrich Syndrome, Selective IgA-deficiency, BTK-deficiency and CD40L-deficiency patients. The information provided by the multicenter evaluation was used to reshape the panel in order to achieve both an optimal efficiency and high reproducibility among the different laboratories.

In one aspect, the invention provides a reagent composition for flow cytometric immunophenotyping of leukocytes comprising fluorochrome-conjugated antibodies directed against one of the following combination of markers:

(a) CD27, CD45RA, CD8, IgD, CD16, CD56, CD4, IgM, CD19, CD3, CD45, and either TCRαβ or TCRγδ, wherein the antibody within the pairs CD8/IgD, CD16/CD56, CD4/IgM and CD19/TCRαβ or CD19/TCRγδ is conjugated to the same fluorochrome, and wherein between different pairs the fluorochromes are distinguishable (referred to as "PID screening tube");
(b) CD27, IgM, CD38, CD5, IgD, CD19, CD21, and CD24 (referred to as "Pre-GC B-cell tube");
(c) CD27, IgM, IgA, IgG, IgD, CD19, CD21, CD38 and optionally IgE; preferably CD27, IgM, IgA, IgE, IgG, IgD, CD19, CD21 and CD38 wherein the composition comprising two distinctly labeled antibodies against IgA and wherein the antibody within the pairs IgE/IgA and IgG/IgA is conjugated to the same fluorochrome and wherein between different pairs the fluorochromes are distinguishable (referred to as "Post-GC B-cell tube");
(d) CD27, IgM, IgG3, IgG2, IgG1, IgD, CD19, CD21, and CD38; the composition comprising two distinctly labeled antibodies against IgG2 and wherein the antibody within the pairs IgG3/IgG2 and IgG1/IgG2 is conjugated to the same fluorochrome and wherein between different pairs the fluorochromes are distinguishable (referred to as "Ig-Isotype B-cell tube-1");
(e) CD27, IgM, IgA2, IgA1, IgG4, IgD, CD19, CD21, and CD38; the composition comprising two distinctly labeled antibodies against IgA1 and wherein the antibody within the pairs IgA1/IgG4 and IgA1/IgA2 is conjugated to the same fluorochrome and wherein between different pairs the fluorochromes are distinguishable (referred to as "Ig-Isotype B-cell tube-2"):
(f) CD62L, CD4, CD45RO, CD31, HLA-DR, CD3, CD8 and either TCRαβ or TCRγδ (referred to as "SCID/RTE tube");
(g) CD27, CD4, CD45RO, CCR7, CD28, CD3, CD8 and either TCRαβ or TCRγδ (referred to as "T-cell subset tube"); or
(h) CD27, CD45RA, CD45, CD16, CD3, CD8, IgD, CD4, IgM, CD56, CD19, CCR7, CD38, either HLA-DR or CD31, and either TRCαβ or TCRγδ, wherein the antibody within the pairs CD8/IgD, CD4/IgM and CD19/TCRαβ or CD19/TCRγδ is conjugated to the same fluorochrome, and wherein between different pairs the fluorochromes are distinguishable (12-color PID screening tube).

Accordingly, the invention provides in one aspect a reagent composition for flow cytometric immunophenotyping of leukocytes comprising twelve distinct fluorochrome-conjugated antibodies conjugated with 8 different fluorochromes, the EuroFlow PID screening tube. This EuroFlow PID Screening tube includes a reagent composition as provided herein that comprises a panel of antibodies directed against the following combinations of markers: CD27, CD45RA, CD8, IgD, CD16, CD56, CD4, IgM, CD19, CD3, CD45, and either TCRαβ or TCRγδ, wherein the antibody within the pairs CD8/IgD, CD16/CD56, CD4/IgM and CD19/TCRαβ or CD19/TCRγδ is conjugated to the same fluorochrome, and wherein between different pairs the fluorochromes are distinguishable (referred to as "PID Screening tube"). In one embodiment, the reagent composition comprises a panel of antibodies directed against one of the following combinations of markers: CD27, CD45RA, CD8, IgD, CD16, CD56, CD4, IgM, CD19, CD3, CD45, and TRCαβ, wherein the antibody within the pairs CD8/IgD, CD16/CD56, CD4/IgM and CD19/TCRαβ is conjugated to the same fluorochrome. In another embodiment, it comprises a panel of antibodies directed against the following combinations of markers: CD27, CD45RA, CD8, IgD, CD16, CD56, CD4, IgM, CD19, CD3, CD45, and TCRγδ, wherein the antibody within the pairs CD8/IgD, CD16/CD56, CD4/IgM and CD19/TCRγδ is conjugated to the same fluorochrome. Thus, the EuroFlow PID Screening tube may consists of an 8-color 14 parameter screening tube (including scatter) that allows detection of the major lymphocyte subsets, which either provides sufficient information for guiding further genetic testing or warrants further analysis of B- and/or T-cell subsets.

The inventors have also designed alternative embodiments comprising either ten or twelve distinct fluorochrome-conjugated antibodies, including those against all the markers described above. For example, also provided is reagent composition as described above which further comprises a fluorochrome-conjugated antibody against the markers CCR7 and/or CD38. Preferably, it comprises antibodies against the markers CCR7 and CD38 (referred to as "10-color PID Screening tube").

In a further aspect, the invention provides a reagent composition comprising a panel of fluorochrome-conjugated antibodies directed against the following combinations of markers: CD27, IgM, CD38, CD5, IgD, CD19, CD21, and CD24 (Pre-GC B-cell tube).

In a still further aspect, the invention provides a reagent composition (Post-GC B-cell tube) comprising a panel of fluorochrome-conjugated antibodies directed against the following combinations of markers: CD27, IgM, IgA, IgG, IgD, CD19, CD21, CD38 and optionally IgE. Preferably, it comprises antibodies against CD27, IgM, IgA, IgE, IgG, IgD, CD19, CD21 and CD38, wherein the composition comprises two distinctly labeled antibodies against IgA and wherein the antibody within the pairs IgE/IgA and IgG/IgA is conjugated to the same fluorochrome and wherein between different pairs the fluorochromes are distinguishable. Antibodies against additional markers may be added. Preferably, the reagent composition further comprises fluorochrome-conjugated antibodies against the markers CD24 and CD5 (referred to as "10-color Pre+Post-GC tube").

In a still further aspect, the invention provides a reagent composition (Ig-Isotype B-cell tube-1), comprising a panel of fluorochrome-conjugated antibodies directed against the following combinations of markers: CD27, IgM, IgG3, IgG2, IgG1, IgD, CD19, CD21, and CD38; and wherein the composition comprises two distinctly labeled antibodies against IgG2 and wherein the antibody within the pairs IgG3/IgG2 and IgG1/IgG2 is conjugated to the same fluorochrome and wherein between different pairs the fluorochromes are distinguishable.

In a still further aspect, the invention provides a reagent composition (Ig-Isotype B-cell tube-2), comprising a panel of fluorochrome-conjugated antibodies directed against the following combinations of markers: CD27, IgM, IgA2, IgA1, IgG4, IgD, CD19, CD21, and CD38; wherein the composition comprises two distinctly labeled antibodies against IgA1 and wherein the antibody within the pairs IgA1/IgG4 and IgA1/IgA2 is conjugated to the same fluorochrome and wherein between different pairs the fluorochromes are distinguishable.

Also provided is a single tube reagent composition for the detection of all Ig-Isotypes. This reagent composition comprises a panel of fluorochrome-conjugated antibodies directed against the following combination of markers: CD27, IgM, IgG3, IgG2, IgG1, IgD, CD19, CD21, CD38, IgA1, IgA2 and IgG4; wherein the composition comprises two distinctly labeled antibodies against IgG2 and two distinctly labeled antibodies against IgA1, and wherein the antibody within the pairs IgG3/IgG2, IgG1/IgG2, IgA1/IgG4, and IgA1/IgA2 is conjugated to the same fluorochrome and wherein between different pairs the fluorochromes are distinguishable (referred to as "10-color Ig-Isotype tube"). This reagent composition can be adapted into a 12-color reagent composition by the further addition of fluorochrome-conjugated antibodies against the markers CD5 and CD24 (referred to as "12-color B-cell tube").

In a still further aspect, the invention provides a reagent composition (SCID/RTE tube), comprising a panel of fluorochrome-conjugated antibodies directed against the following combinations of markers: CD62L, CD4, CD45RO, CD31, HLA-DR, TCRγδ or TCRαβ, CD3 and CD8. This tube finds its use among others in the analysis of a sample obtained from a subject that tested positively in a screening test for SCID. The suspicion of (S)CID can for example be based on routine neonatal screening using the so-called T-cell Receptor Excision circles (TRECs), which are circular DNA fragments generated during T-cell receptor rearrangement. In healthy neonates, TRECs are made in large numbers, while in infants with SCID, they are barely detectable.

In a still further aspect, the invention provides a reagent composition (T-cell subset tube), comprising a panel of fluorochrome-conjugated antibodies directed against the following combinations of markers: CD27, CD4, CD45RO. CCR7, CD28, TCRγδ or TCRαβ, CD3 and CD8, or the markers CD27, CD4, CD45RO, CCR7, HLA-DR. TCRγδ or TCRαβ, CD3 and CD8.

In yet a further aspect, the invention provides a reagent composition (12-color PID screening tube), comprising a panel of fluorochrome-conjugated antibodies directed against the following combinations of markers: CD27, CD45RA, CD45, CD16, CD3, CD8, IgD, CD4, IgM, CD56, CD19, CCR7, CD38, either HLA-DR or CD31, and either TCRαβ or TCRγδ, wherein the antibody within the pairs CD8/IgD, CD4/IgM and CD19/TCRαβ or CD19/TCRγδ is conjugated to the same fluorochrome, and wherein between different pairs the fluorochromes are distinguishable. In one embodiment, the reagent composition comprises antibodies directed against CD27, CD45RA, CD45, CD16, CD3, CD8, IgD, CD4, IgM, CD56, HLA-DR, CD19, CCR7, CD38 and TCRαβ, wherein the antibody within the pairs CD8/IgD, CD4/IgM and CD19/TCRαβ is conjugated to the same fluorochrome. In another embodiment, the reagent composition comprises antibodies directed against CD27, CD45RA, CD45, CD16, CD3, CD8, IgD, CD4, IgM, CD56, HLA-DR, CD19, CCR7, CD38 and TCRγδ, wherein the antibody within the pairs CD8/IgD, CD4/IgM and CD19/TCRγδ is conjugated to the same fluorochrome.

In a preferred embodiment, a reagent composition of the invention comprises monoclonal antibodies. CD stands for cluster designation and is a nomenclature for the identification of specific cell surface antigens defined by monoclonal antibodies. (Monoclonal) antibodies against the indicated markers can be commercially obtained from various companies, including Becton Dickinson (BD) Biosciences, Dako, Beckman Coulter, CYTOGNOS, Caltag, Pharmingen, Exbio, Sanquin, Invitrogen, and the like.

The expression "wherein between different pairs the fluorochromes are distinguishable wherein the antibody within either one of the pairs is conjugated to the same fluorochrome" is meant to indicate that both antibodies of the first pair are conjugated to fluorochrome A and that both antibodies of the second pair are conjugated to fluorochrome B. Thus, within each pair the fluorochromes are the same but between different pairs the fluorochromes are distinguishable. Each of the reagent compositions can be used as such, e.g. for the screening of an immunodeficiency disease.

The invention thus also relates to diagnostic kits comprising one or more reagent compositions. However, the compositions are also advantageously used in combination with one or more further reagent compositions, in particular reagent compositions designed for the further screening and classification of the disease. The expression "in combination with" does not refer to the physical combination or mixing of the reagent compositions, but to their application in separate (consecutive or parallel) analysis steps and combination of the data thus obtained.

Therefore, the invention also relates to a set of at least two reagent compositions comprising distinct fluorochrome-conjugated antibodies, said set comprising a first reagent composition as described herein above, and at least one further reagent composition as described herein above. Thus, both reagent compositions comprise a distinct panel of antibodies, although some antibodies might be present in both compositions.

Figure 1B:
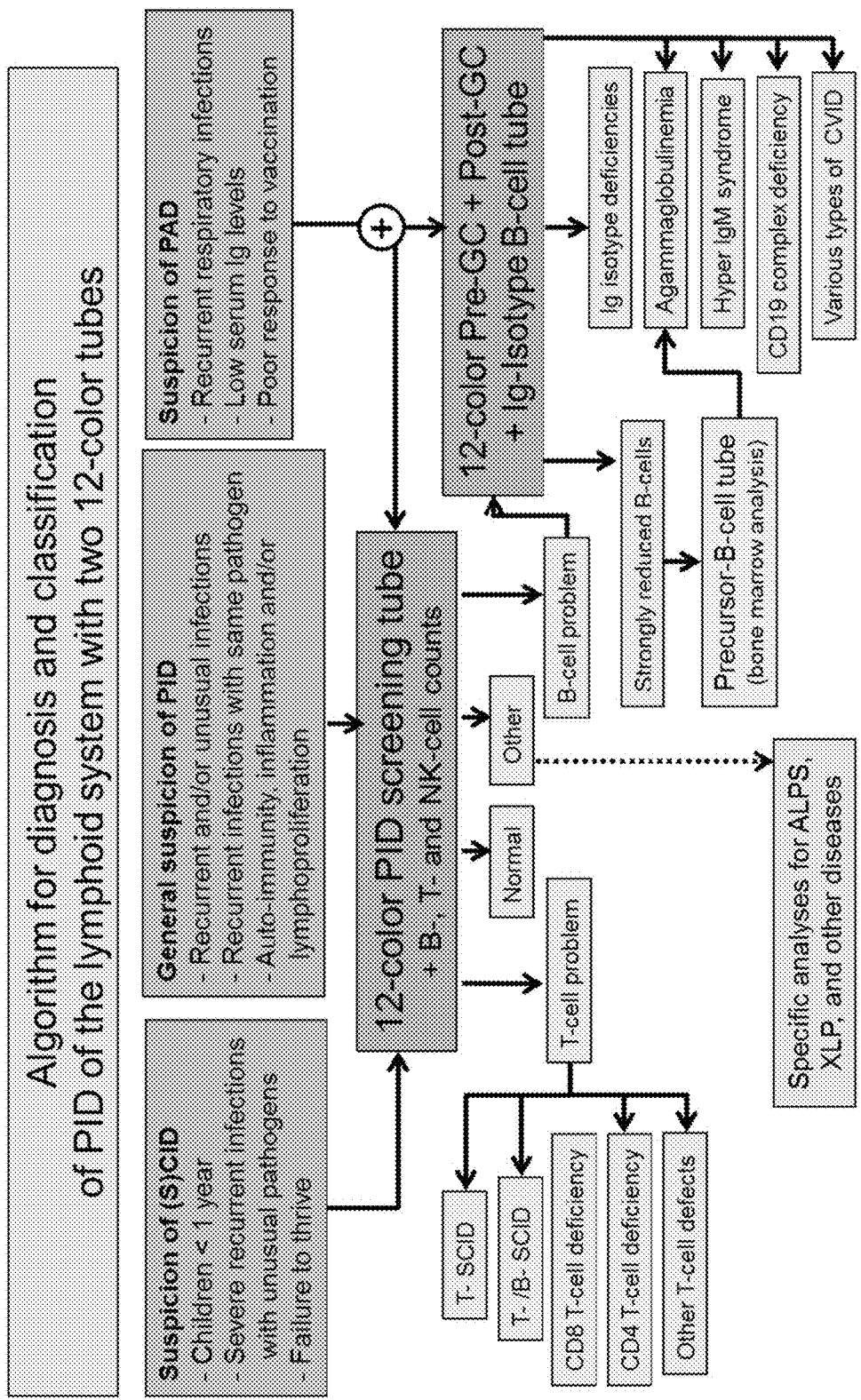

For example, the EuroFlow PID Screening tube used in combination with a characterization tube can involve two separate analytical steps on separate aliquots of the same biological sample, each using one of the reagent compositions, followed by data recording and evaluation (see FIG. 1). In one embodiment, the PID diagnostic algorithm comprises a Screening tube and a subsequent set of Classification tubes (FIG. 1). The PID Screening tube aims at the identification, characterization and enumeration of lymphocytes and other leukocytes in primary and secondary lymphoid and hematopoietic tissues, such as B-, T- and NK-cells, antigen-presenting cells, phagocytes and plasma cells, this includes pre- and post-germinal center (GC) B-cells. Depending on the result of the PID Screening tube, additional tubes designed for a more detailed analysis of B-cell and T-cell subsets can be used for further classification of PID. The Pre-GC. Post-GC, and Ig-Isotype B-cell tubes aim at the identification, characterization and enumeration of B-cell subsets for the evaluation of B-cell differentiation defects associated with both maturation blocks and specific defects in the production of one or several immunoglobulin subclasses (e.g. CVID). Finally, the T-cell memory/effector subset tube and SCID/RTE antibody tube aim at the identification, characterization and enumeration of T-cell subsets for the evaluation of alterations in T-cell production, differentiation and/or activation (e.g. SCID).

It is very convenient if the panel of distinct fluorochromes is essentially the same for each of the reagent compositions, and that up to eight, ten or twelve different fluorochromes are used in total.

In one embodiment, each reagent composition comprises antibodies conjugated to (1) pacific blue (PacB), brilliant violet 421 (BV421) or Horizon V450; (2) pacific orange (PacO), Horizon V500 (HV500), BV510, Khrome orange (KO) or OC515, (3) Horizon BB515, fluorescein isothiocyanate (FITC) or Alexa488, (4) phycoerythrin (PE), (5) peridinin chlorophyl protein/cyanine 5.5 (PerCP-Cy5.5), PerCP or PE-TexasRed, (6) phycoerythrin/cyanine7 (PE-Cy7), (7) allophycocyanine (APC) or Alexa647, and (8) allophycocyanine/hilite 7 (APC-H7), APC-Cy7, Alexa680, APC-A750, APC-C750 or Alexa700.

In another embodiment, each reagent composition comprises antibodies conjugated to (1) brilliant violet 421, (2) brilliant violet 510 (BV510), (3) brilliant violet 650 (BV650), (4) brilliant violet 786 (BV786), (5) fluorescein isothiocyanate (FITC), (6) peridinin chlorophyl protein/ cyanine 5.5 (PerCP-Cy5.5), (7) to phycoerythrin (PE), (8) phycoerythrin/cyanine7 (PE-Cy7), (9) allophycocyanine (APC), and (10) allophycocyanine/H7 (APC-H7), APC-C750 or APC-Alexa750.

A further aspect of the invention relates to a diagnostic kit for flow cytometric immunophenotyping of leukocytes comprising a reagent composition or at least one set of reagent compositions according to the invention, optionally together with instructions for use, buffer, and/or control samples. For example, provided is a diagnostic kit for the diagnosis of primary immunodeficiences (PID), preferably PID of the lymphoid system. In another embodiment, the kit is used for the identification of alterations in leukocyte subsets in an immunological disease, preferably for immune monitoring of patients with infections, autoimmune disease, allergy, after transplantation, vaccination or other type of immune therapy including antibody therapy.

Preferred combinations of reagents for use in a kit of the invention include the following (see tables 1, 2 and 3 for the combination of antibodies in each tube):
Tubes #2 and #3
Tubes #4 and #5
Tubes #2, #3, #4 and #5
Tubes #1, #2 and #3
Tubes #1, #4 and #5
Tubes #1, #2, #3, #4 and #5
Tubes #6 and #7
Tubes #1 and #7
Tubes #1, #6 and #7
Tubes #9 and #10
Tubes #8, #9 and #10
Tubes #8 and #11
Tubes #12 and #13
Tube #1, #2, #3, #4, #5, #6, #7
And any combination thereof Also provided is a multi-color flow cytometric method for immunophenotyping of leukocytes, comprising the steps of:
(a) providing a biological sample comprising leukocytes;
(b) contacting a first aliquot of said sample with a first reagent composition of a set according to the invention, and contacting at least a second aliquot of said sample with a further reagent composition of said set;
(c) analyzing leukocytes in said aliquots in a flow cytometer; and
(d) storing and evaluating the data obtained.

The sample can be any sample known of suspected to contain leukocytes. Exemplary biological samples include peripheral blood, bone marrow, tissue sample such as lymph nodes, adenoid, spleen, or liver, or other type of body fluid such as cerebrospinal fluid, vitreous fluid, synovial fluid, final needle aspirate, pleural effusions and ascitis. In a preferred embodiment, the sample is a peripheral blood sample. In a specific aspect, the biological sample is obtained from an individual with SCID, preferably from an individual which tested positive in a routine neonatal screening using the so-called TREC assay based on detection of circular DNA fragments generated during T-cell receptor rearrangement. Accordingly, the invention also provides a multi-color flow cytometric method for immunophenotyping of leukocytes, comprising the steps of:
(a) identifying an individual testing positive for SCID using a TREC assay;
(b) obtaining from said SCID-positive individual a biological sample comprising leukocytes;
(c) contacting an aliquot of said sample with a reagent composition of the invention, in particular the SCID/RTE tube and/or the screening tube, and contacting at least a second aliquot of said sample with a further reagent composition of said set;
(d) analyzing leukocytes in said aliquots in a flow cytometer; and
(e) storing and evaluating the data obtained.

The method advantageously comprises combining the immunophenotypic information of the selected cell populations from multiple tubes according to the so-called nearest neighbor calculations in which individual cells from one aliquot of a sample are matched with corresponding individual cells from another aliquot of the same sample, according to their markers and scatter profile.

Preferably, the method comprises the use of software for data integration and multidimensional analysis of flow cytometry files. For example, the antibody panels according to the invention can be used in combination with the INFINICYT software tools or any other software programs, which are commercially available. The INFINICYT software is based on recently described procedures for generating files with an unlimited number of parameters through merging data files and calculating the information derived from the measurement of markers in one sample aliquot to the individual cells measured in other aliquots of the same sample, using different combinations of antibody reagents which only have partial overlap (Orfao et al, U.S. Pat. No. 7,321,843), as well as for comparisons between different samples or different groups of samples (Orfao et al, U.S. Pat. No. 7,507,548).

These multi-color immunostainings can be performed according to the so-called EuroFlow protocols as described by Van Dongen et al. (Leukemia 2012; 26: 1908) and by Kalina et al. (Leukemia 2012; 26: 1986), or that are available via the EuroFlow webpage (www.EuroFlow.org.)

DETAILED DESCRIPTION

1. Flow Cytometric Analysis and Exemplary Composition of the Antibody Panels in Eight, Ten or Twelve Distinct Fluorochromes The panels herein proposed comprising eight distinct fluorochrome-conjugated antibodies can be reduced to a lower number of tubes providing comparable information with combinations of either ten or twelve distinct fluorochrome-conjugated antibodies, as described below.

1.1. Flow Cytometric Analysis and Exemplary Composition of the Panels Comprising Antibodies Conjugated with Eight Distinct Fluorochromes The EuroFlow PID Screening reagent composition was designed and approved for evaluation of several suspected clinical conditions, such as recurrent or persistent infections, developmental delay, presence of low serum immunoglobulin levels, and failure of antibody development on exposure to antigens. These reagents aim at the detailed dissection of the circulating leukocyte subsets including B-cells, T-cells. NK-cells, monocytes, dendritic cells, basophils, neutrophils and eosinophils. Additionally B-cells and T-cells can be classified into different functional/maturation subsets. Accordingly, B-cells are divided into pre-GC B-cells (including both immature/transitional and naïve B-cells), unswitched and switched memory B-cells and plasmablasts/plasma cells. The T-cell compartment can be divided into different functional subsets according to the TCRγδ or TCRαβ, CD4 and CD8 expression. These T-cell subsets can be further subdivided according to their maturation stage in naïve, memory, effector and effector RA$^+$ cells.

The composition of an exemplary PID Screening tube is provided in Table 1. This reagent composition detects defects in the production of B-cells. T-cells and NK-cells, together with alterations (defective but also increased production) in the production of monocytes, dendritic cells, neutrophils, eosinophils and basophils. However, in most of the cases this tube does not allow the precise classification of the T-cell and B-cell detected defects. This typically needs further characterization with additional tubes (FIG. 1).

The Pre-GC, Post-GC and Ig-Isotype B-cell antibody panels consist of combinations devoted to in-depth characterization of defects related with decreased or absent immunoglobulin levels in the serum and/or other tissues (e.g. mucosa). For certain PID, especially the antibody deficiencies with defects in the B-cell system, more detailed analysis is required to study in detail the B-cell subpopulations. B-cells originate from bone marrow stem cells and differentiate via multiple differentiation stages into immature B-cells that leave the bone marrow and enter the periphery, including the blood that is analyzed with flow cytometric analysis in the diagnosis of PID. In the periphery, the B-cell encounters antigen after which it can undergo a germinal center (GC) reaction. Consequently, in blood, B-cells are present that did not yet undergo a germinal center reaction (pre-GC B-cells) or that already underwent a germinal center reaction (post-GC B-cells).

These post-GC subsets can be further subdivided according to their Ig isotypes: IgM, IgD, IgE, IgG (including IgG1, IgG2, IgG3, IgG4), and IgA (including IgA1, IgA2), or IgM, IgD, IgG (including IgG1, IgG2, IgG3, IgG4), and IgA (including IgA1, IgA2). These panels include markers for the identification of defects associated with the production of different pre-GC B-cell subsets, including immature/transitional, naive CD5+ and naive CD5− B-cells, the production of post-GC subsets, including memory B-cells and plasmablasts/plasma cells, and the classification of both memory B-cells and plasmablasts/plasma cells according to the total isotype in a single tube (IgM, IgD, IgG, IgA, IgE) or in another embodiment IgM, IgD, IgG and IgA, and/or the specific immunoglobulin subclass expressed with the combination of two tubes (IgM, IgD, IgG1, IgG2, IgG3, IgG4, IgA1, and IgA2).

For PID of the lymphoid system, detailed analysis of T-cell subsets is also preferred for making a correct diagnosis. For severe combined immunodeficiency (SCID) the T-cells present in peripheral blood might not be autologous, but might be transplacentally derived maternal T-cells. It is important to make a distinction between maternal T-cells and autologous T-cells that recently emigrated from the thymus, called recent thymic emigrants (RTE). This requires an additional flow cytometric analysis that is only necessary if SCID is suspected, for instance on the basis of routine (neonatal) screening based on detection of the so-called T-cell Receptor Excision circles (TRECs). The invention accordingly relates to two tubes aimed at the identification of these and other additional T-cell subsets: one for analysis of T-cell subsets and one specific SCID/RTE tube.

Suitable fluorochromes for conjugating antibodies for use in the present invention against the recited markers are known in the art. As will be understood, the fluorochromes used within a reagent composition should be distinguishable from each other by flow cytometry. The fluorochromes are preferably selected for brightness, limited spectral overlap and limited need for compensation, stability, etc. (see: Kalina et al. Leukemia 2012; 26: 1986).

In Table 1 of the present application the following panel of fluorochromes is of particular use: (1) pacific blue (PacB), brilliant violet 421 (BV421) or Horizon V450, (2) pacific orange (PacO), Horizon V500 (HV500), BV510, Khrome orange (KO) or OC515, (3) Horizon BB515, fluorescein isothiocyanate (FITC) or Alexa488, (4) phycoerythrin (PE), (5) peridinin chlorphyl protein/cyanine 5.5 (PerCP-Cy5.5), PerCP or PE-Texas-Red, (6) phycoerythrin/cyanine7 (PE-Cy7), (7) allophycocyanine (APC) or Alexa647, and (8) allophycocyanine/hilite 7 (APC-H7), APC-Cy7, Alexa680, APC-A750, APC-C750 or Alexa700.

TABLE 1

Exemplary 8-color reagent compositions

| | F1 | F2 | F3 | F4 | F5 | F6 | F7 | F8 |
|---|---|---|---|---|---|---|---|---|
| #1 Screening tube | CD27 | CD45RA | CD8 IgD | CD16 CD56 | CD4 IgM | CD19 TCRγδ or TCRαβ | CD3 | CD45 |
| #2 Pre-GC tube | CD27 | IgM | CD38 | CD5 | IgD | CD19 | CD21 | CD24 |
| #3 Post-GC tube | CD27 | IgM | (IgE)* IgA | IgG (IgA)* | IgD | CD19 | CD21 | CD38 |
| #4 Ig-Isotype tube 1 | CD27 | IgM | IgG3 IgG2 | IgG1 IgG2 | IgD | CD19 | CD21 | CD38 |
| #5 Ig-Isotype tube 2 | CD27 | IgM | IgA1 IgG4 | IgA1 IgA2 | IgD | CD19 | CD21 | CD38 |
| #6 T-cell subset tube | CD27 | CD28 | CD8 | CCR7 | CD4 | TCRγδ or TCRαβ | CD3 | CD45RO |
| #7 SCID/RTE | CD62L | HLA-DR | CD8 | CD31 | CD4 | TCRγδ or TCRαβ | CD3 | CD45RO | asterisk *denotes that the composition may contain an antibody against IgE and a second antibody against IgA The invention also relates to a method for flow cytometric diagnosis of PID, comprising the steps of providing a biological sample from a human subject and contacting at least a portion (aliquot) of the sample with a reagent composition provided herein. Any type of sample known or suspected to contain leukocytes may be used directly, or after lysing non-nucleated red cells, or after density centrifugation, or after cell sorting procedures.

1.2. Flow Cytometric Analysis and Composition of the Panels Comprising Antibodies Conjugated with Ten Distinct Fluorochromes Alternative panels comprising antibodies conjugated with ten distinct fluorochromes have been designed providing information comparable to that from the tubes of Section 1.1. All the information contained in both the pre-GC and post-GC B-cell tubes from Section 1.1 panels is here contained in a single tube (Pre-GC+Post-GC B-cell tube). Also, the classification of memory B-cells and plasmablast/plasma cells according to the immunoglobulin subclass expressed (IgM, IgD, IgG1, IgG2, IgG3, IgG4, IgA1, and IgA2 in the two Ig-isotype B-cell tubes from the 1.1 panels—) can be performed in a single tube (Ig-Isotype B-cell tube). Also the SCID/RTE tube and T-cell subset tubes are now combined into one T-cell subset tube, which contains the CD31 and CD61L markers. Finally, the EuroFlow Screening tube offers a better discrimination of T-cell maturation subsets based on CCR7 expression (e.g. central vs. peripheral memory), while the inclusion of CD38 allows for the discrimination of immature/transitional vs. naive B-cells and helps to reach a more accurate identification of plasmablasts/plasma cells.

In Table 2 of the present application, fluorochrome number 1 correspond to brilliant violet 421 (BV421), number 2 to brilliant violet 510 (BV510), number 3 to brilliant violet 650 (BV650), number 4 to brilliant violet 786 (BV786), number 5 to fluorescein isothiocyanate (FITC), number 6 to peridinin chlorophyl protein/cyanine 5.5 (PerCP-(Cy5.5), number 7 to phycoerythrin (PE), number 8 to phycoerythrin/cyanine7 (PE-Cy7), number 9 to allophycocyanine (APC), and number 10 to allophycocyanine/H7 (APC-H7). APC-C750 or APC-Alexa750. Such fluorochrome combination is just used as an example and should not limit the use of other combinations of compatible fluorochromes, also contained in the present invention.

TABLE 2

Exemplary 10-color reagent compositions

| | F1 | F2 | F3 | F4 | F5 | F6 | F7 | F8 | F9 | F10 |
|---|---|---|---|---|---|---|---|---|---|---|
| #8 Screening tube | CD27 | CD45RA | CD45 | CD3 | CD8 IgD | CD4 IgM | CD16 CD56 | CD19 TCRγδ or TCRαβ | CCR7 | CD38 |
| #9 Pre-GC + post-GC tube | CD27 | IgM | CD24 | CD19 | IgE IgA | CD5 | IgG IgA | IgD | CD21 | CD38 |
| #10 Ig-Isotype tube | CD27 | IgM | CD24 | CD19 | IgG3 IgG2 | IgA1 IgA2 | IgG1 IgG2 | IgD | IgA1 IgG4 | CD38 |
| #11 T-cell subset tube | CD27 | HLA-DR | CD45RO | CD3 | CD8 | CD4 | CCR7 | TCRγδ or TCRαβ | CD31 | CD62L |

1.3. Flow Cytometric Analysis and Composition of the Panels Comprising Antibodies Conjugated with Twelve Distinct Fluorochromes Alternative reagent compositions comprising antibodies conjugated to twelve distinct fluorochromes have been designed providing information comparable to that from the tubes of the 1.1 panels described above. All the information contained in both the Pre-GC. Post-GC and Ig-Isotype tubes from the 1.1 and 1.2 panels is here contained in a single tube (B-cell tube). Also, together with the extra information provided by the EuroFlow PID Screening tube from the 1.3 panels, the twelve color EuroFlow PID tube can be used for the identification of RTE T-cells, improving the analysis of the SCID patients, and allows for the discrimination of NK-cell subsets based on CD16 vs. CD56 expression.

In the Table 3 of the present application, fluorochrome number 1 corresponds to brilliant violet 421 (BV421), number 2 to brilliant violet 510 (BV510), number 3 to brilliant violet 650 (BV650), number 4 to brilliant violet 711 (BV711), number 5 to brilliant violet 786 (BV786), number 6 to fluorescein isothiocyanate (FITC), number 7 to peridinin chlorophyl protein/cyanine 5.5 (PerCP-Cy5.5), number 8 to phycoerythrin (PE), number 9 to PE-CF594, number 10 to phycoerythrin/cyanine7 (PE-Cy7), number 11 to allophycocyanine (APC), and number 12 to allophycocyanine/H7 (APC-H7), APC-C750 or APC-Alexa750. Such fluorochrome combination is just used as an example and should not limit the use of other combinations of compatible fluorochromes, also contained in the present invention.

This analysis was used to define in a n-dimensional space the best principal component analysis 1 (PC1) vs. PCA2 representation to discriminate these subsets. The PCA representation of the data is resumed in 2× Standard Deviation (SD) curves to be used as a reference for supervised automatic analysis of the samples.

Figure 3:
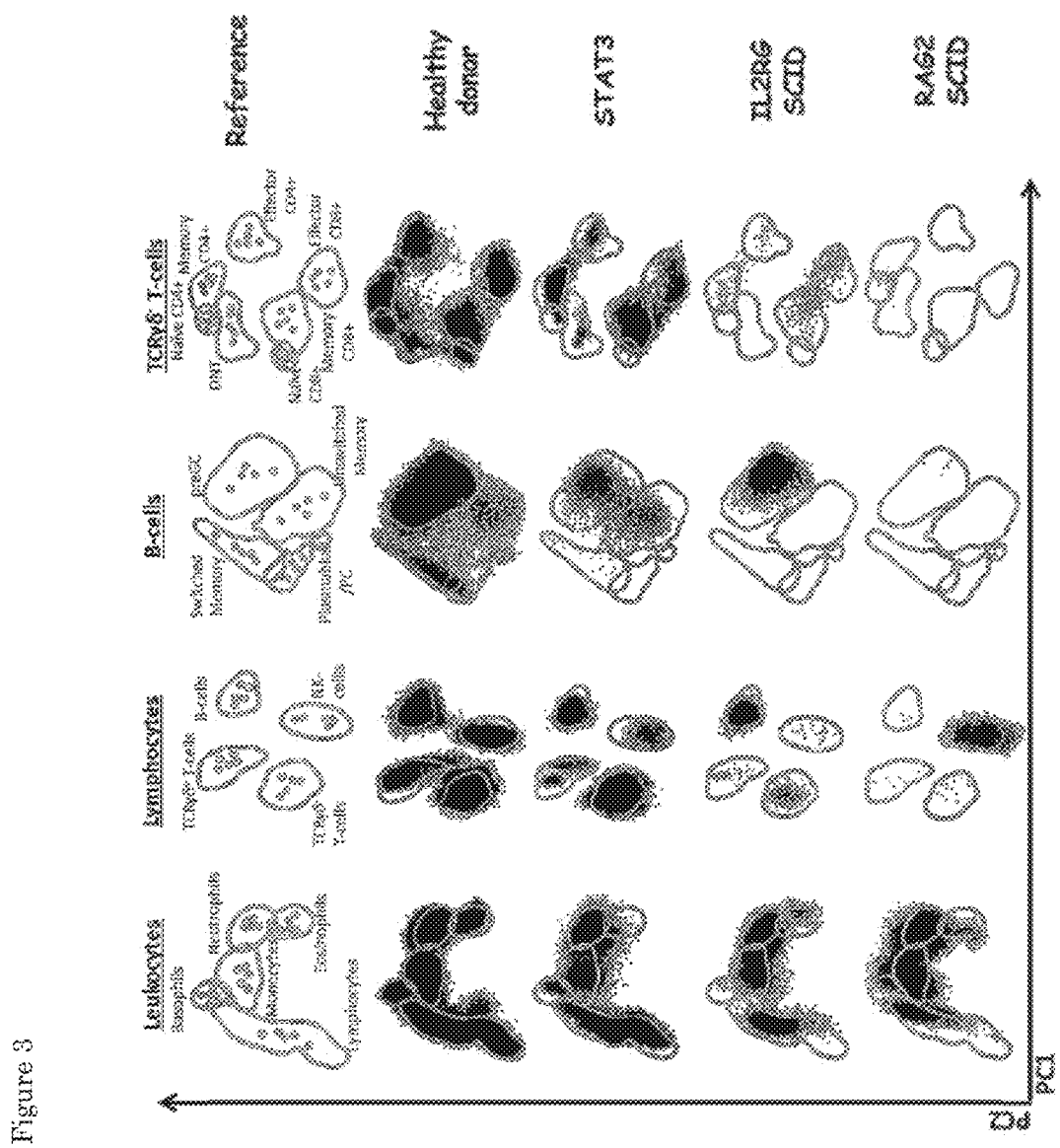

FIG. 3. Application of principal component analysis (PCA) representation of the distinct subsets of leukocytes present in peripheral blood (PB) from reference data files (upper panel) for the supervised analysis of PB samples from healthy donors and primary immunodeficiency patients analyzed with the PID Screening combination of markers.

Reference principal component analysis 1 (PC1) vs. PCA2 representation were generated from 5 healthy donors data files (upper panels) analyzed with the EuroFlow PID Screening combination of markers. Different samples were analysed against the reference PC1 vs. PC2 prototype representations defined on the basis of the distribution of peripheral blood subsets in the five healthy donors stained

TABLE 3

Exemplary 12-color reagent compositions

| | F1 | F2 | F3 | F4 | F5 | F6 | F7 | F8 | F9 | F10 | F11 | F12 |
|---|---|---|---|---|---|---|---|---|---|---|---|---|
| #12 Screening tube | CD27 | CD45RA | CD45 | CD16 | CD3 | CD8 IgD | CD4 IgM | CD56 | HLA-DR or CD31 | CD19 TCRγδ or TCRαβ | CCR7 | CD38 |
| #13 B-cell tube | CD27 | IgM | CD24 | CD5 | CD19 | IgG3 IgG2 | IgA2 IgA1 | IgG1 IgG2 | IgD | CD21 | IgA1 IgG4 | CD38 |

LEGEND TO THE FIGURES

FIG. 1. Algorithm of the strategy for flow cytometric immunophenotyping for screening and classification of primary immunodeficiencies (PID). Panel A. On the basis of several entries of clinical and laboratory parameters, blood samples of patients suspected to have PID are screened with the 8- or 10-color PID Screening tube. Based on the obtained results, additional 8-color or 10-color T- and/or B-cell Classification tubes are applied in a stepwise fashion. In case of suspicion of (S)CID, both the PID screening tube and the two T-cell tubes (SCID/RTE and T-cell subset tube) can be applied together ("T-cell branch" on the left hand side). In case of suspicion of PAD, both the PID screening tube and the Pre-GC+Post-GC tube(s) can applied together, optionally followed by analysis using Ig-Isotype tube(s) ("B-cell branch on the right hand side). If the clinical symptoms are clear enough, the PID screening tube can be omitted. Panel B. 12-color variant of the EuroFlow diagnostic algorithm, consisting of two 12 color tubes: the PID Screening tube, which also includes the T-cell subset analysis, and the B-cell Classification tube, which combines the Pre-GC, Post-GC, and Ig-Isotype analyses. Please note that the precursor-B-cell tubes are not included in this patent application, because several informative ≥8-color tubes have already been proposed (Van Dongen et al. Leukemia 2012; 26: 1986). Abbreviations: GC, germinal center; PAD, primary antibody deficiency; RTE, recent thymic emigrant; SCID, severe combined immunodeficiency.

Figure 2:
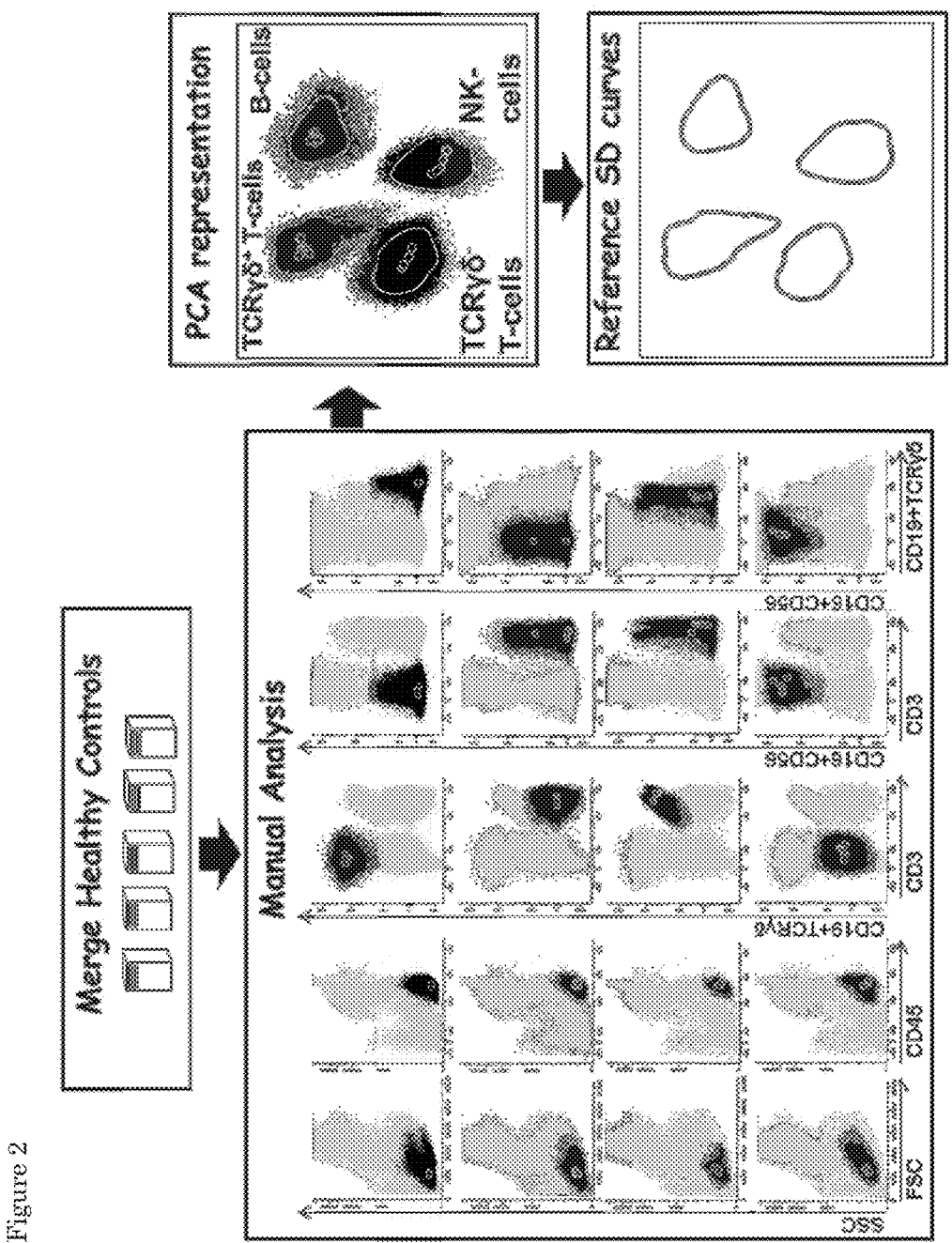

FIG. 2. Generation of a reference principal component analysis 1 (PC1) vs. PCA2 representation in a n-dimensional space for the discrimination of the lymphocytes subsets identified with the PID screening combination of markers.

Data files from 5 healthy donors were merged and lymphocytes subsets of interest identified using bivariate plots.

including: one healthy donor, one patient with mutated STAT3, and two SCID patients with different genetic defect: IL2 receptor gamma chain (IL2RG) and recombination activating gene 2 (RAG2), all samples stained and acquired under identical/comparable conditions.

Figure 4:
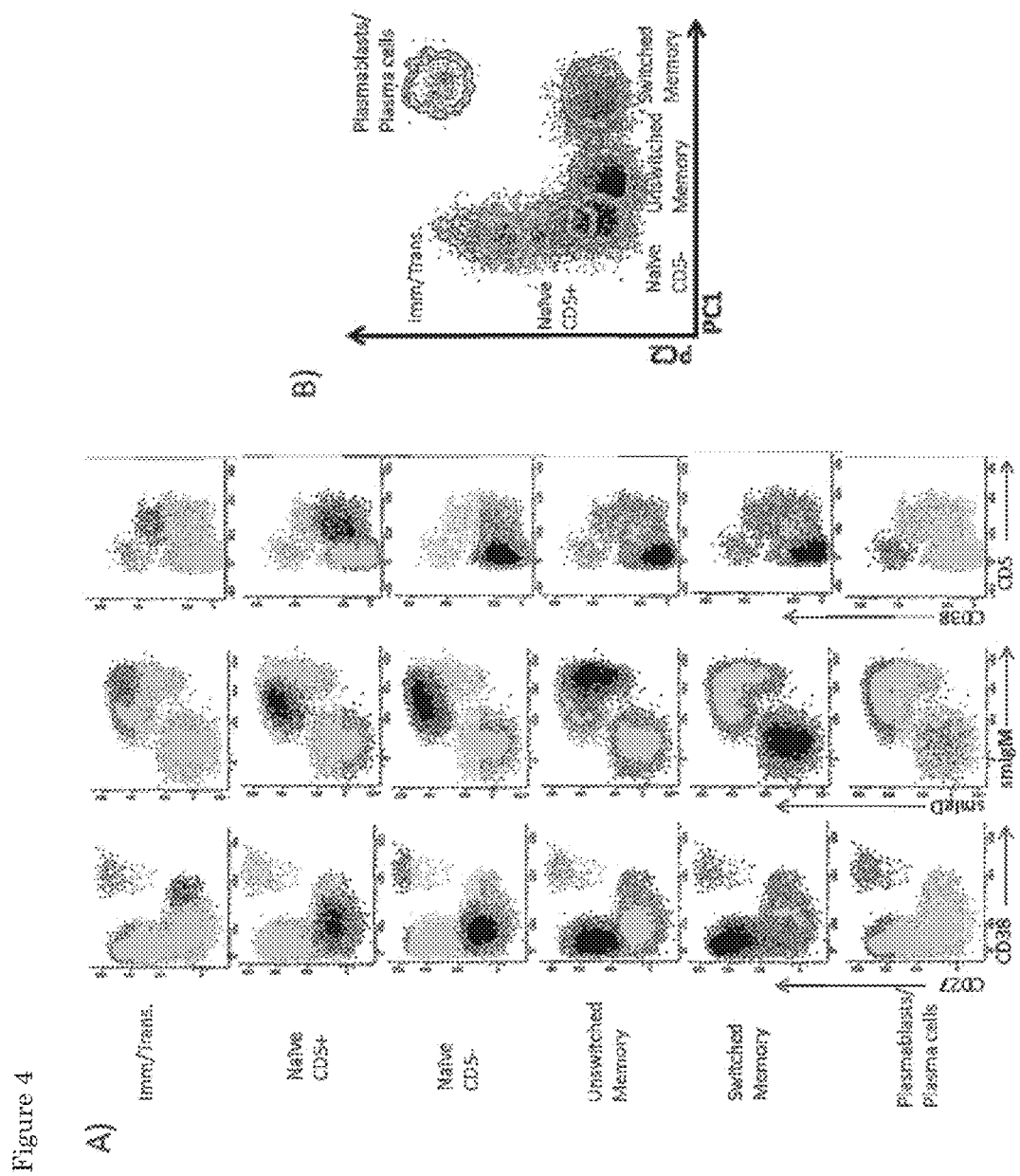

FIG. 4: Identification with the Pre-GC tube combination of markers of major subsets of circulating peripheral blood (PB) B-cells using 2-dimensional plots vs. n-dimensional principal component analysis (PCA).

Analysis of circulating B-cell (FS/SS$^{lo}$CD19) maturation subsets identified within 2×10$^6$ PB leukocytes using the markers from the Pre-GC tube: Immature (CD5$^+$ CD27$^-$ CD38$^{++}$ smIgM$^{++}$ smIgD$^+$), CD5$^+$ and CD5$^-$ naïve B-cells (CD27$^-$ CD38$^{+d}$ smIgM$^+$ smIgD$^{++}$), Ig non-switched and Ig-switched memory B-cells (CD5$^-$ CD27$^+$ CD38$^-$ smIgM$^+$ smIgD$^{++}$ and CD5$^-$ CD27$^{+/-}$ CD38$^-$ smIgM$^-$ smIgD$^-$, respectively), and plasma cells (CD5$^-$ CD27$^{++}$ CD38$^{+++}$). Panel A shows the identification of biologically relevant subsets of B-cells using the minimum number of bivariate plots required for a 5 marker-combination (three bivariate plots/cell population) vs. B) a principal component 1 (PC1) vs. PC2 representation of a 5-dimensional space.

Figure 5:
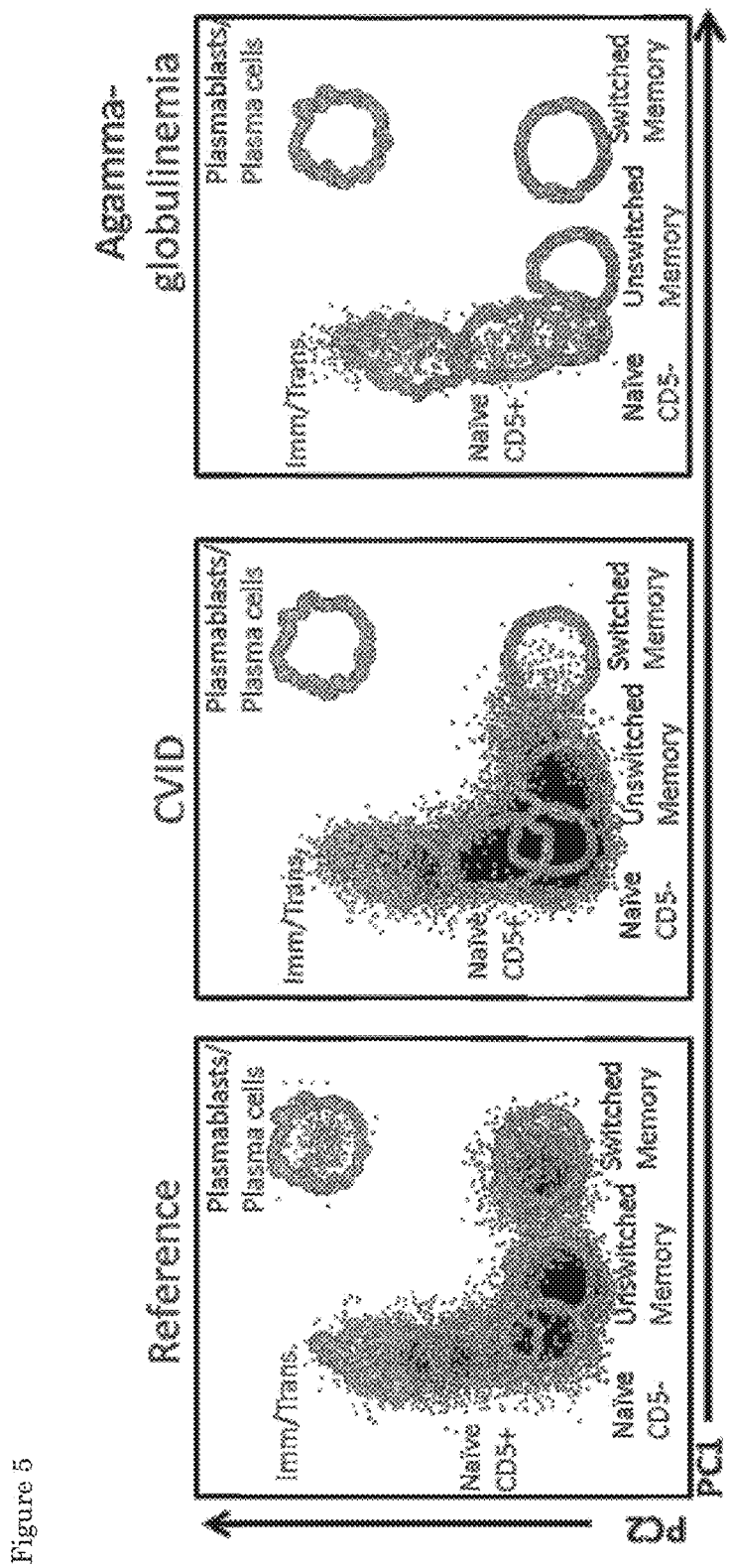

FIG. 5: Principal component analysis (PCA) representation of the distinct subsets of B-cells present in peripheral blood (PB) from a normal/reference sample (panel A) and PB samples from primary immunodeficient patients with altered distribution analyzed with the Pre-GC tube.

Analysis of the distribution of peripheral blood B-cells in patients diagnosed of common variable immunodeficiency (CVID) and agammaglobulinemia, is shown against reference PC1 vs. PC2 prototype representation defined on the basis of the distribution of PB B-cell subsets from six healthy donors stained with the Pre-GC tube and acquired under identical/comparable conditions.

Figure 6:
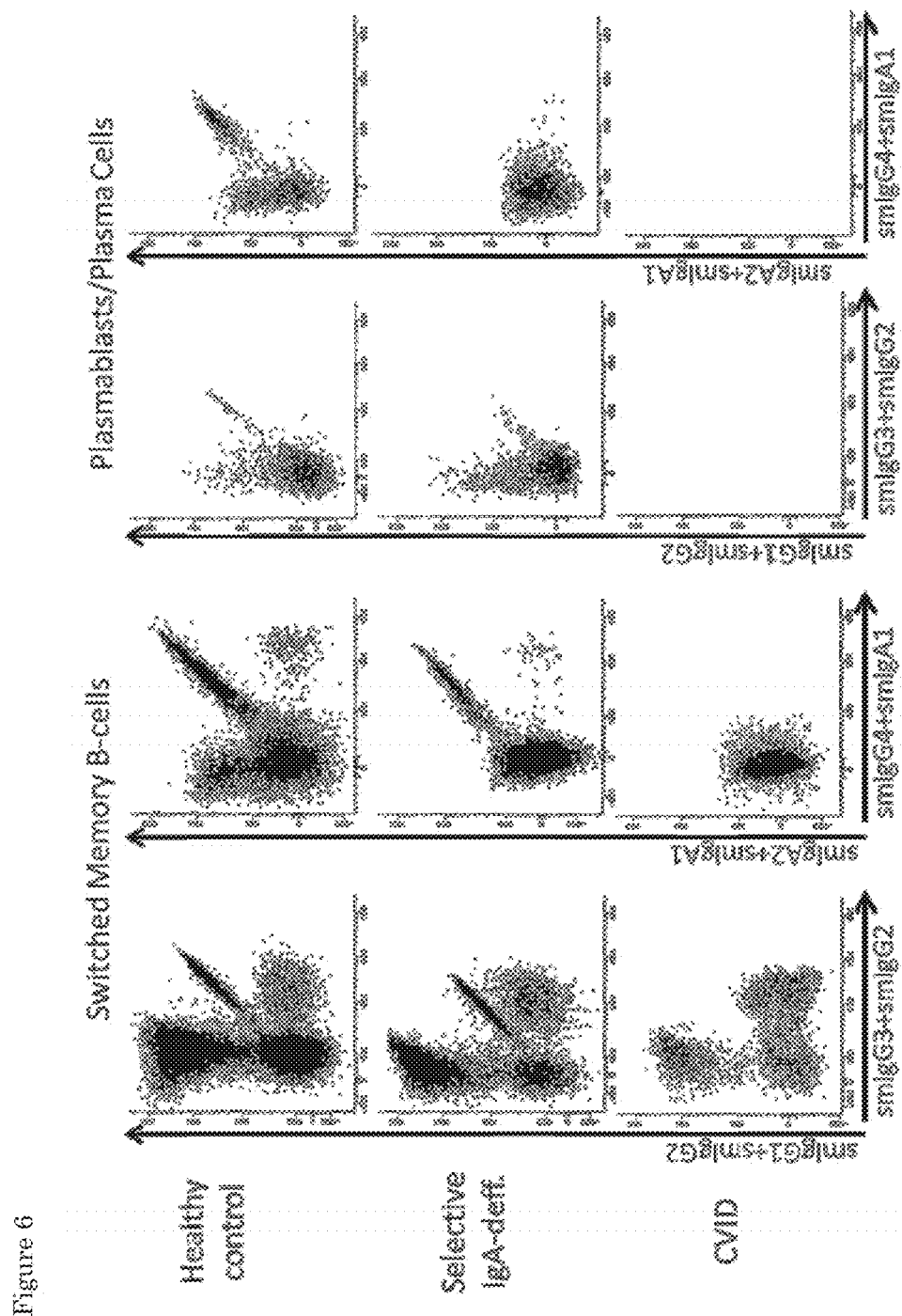

FIG. 6: Application of the isotype tube for the dissection of switched memory B-cells and plasmablasts/plasma cells in peripheral blood from healthy donors and primary immunodeficient patients.

Distribution of switched memory B-cells (smIgMD$^-$ CD19$^+$CD38$^-$) and plasmablasts/plasma cells (CD19$^+$ CD27$^{++}$CD38$^{+++}$) according to the surface membrane (sm) expression of the different subclasses of immunoglobulin heavy chain (IgG1, IgG2, IgG3, IgG4, IgA1, and IgA2) in 5×10$^6$ peripheral blood leukocytes analyzed with the Isotypes tube in samples from a healthy adult (upper panels), from a selective IgA-deficient individual (middle panels) and from a CVID patients (lower panels). No plasmablasts/plasma cells were detected in the peripheral blood from the CVID patient in a frequency higher than 0.001 cells/µL.

Figure 7:
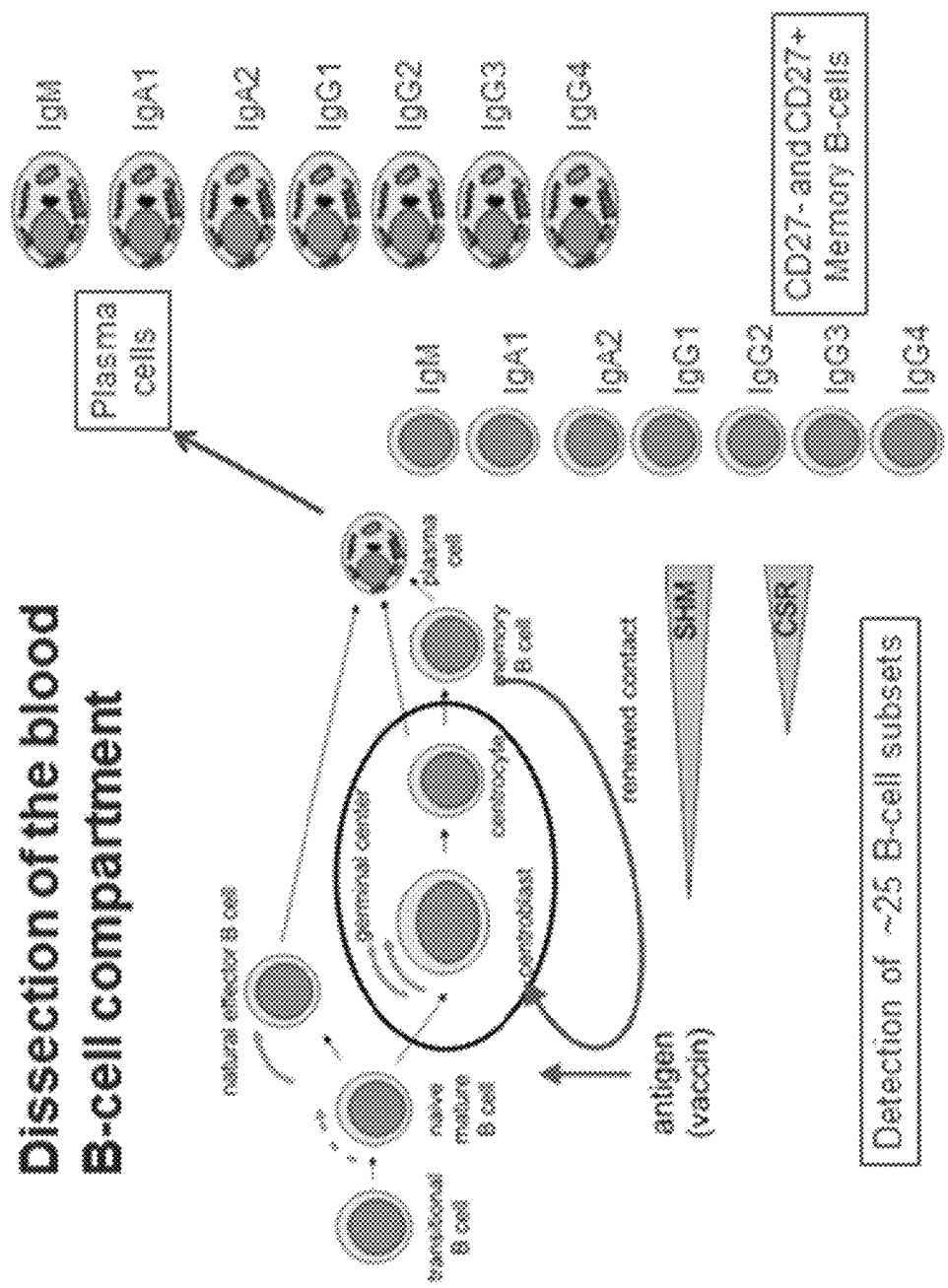

FIG. 7. Dissection of the blood B-cell compartment with the 12-color B-cell type (including the IGH isotype detection), resulting in the detection and quantitation of ~25 different B-cell subsets (naive B-cell subsets, memory B-cell subsets, and plasma cell subsets).

EXPERIMENTAL SECTION

The power of the multicolor flow cytometric approach disclosed herein is based on the combination of sets of markers and the usage of multivariate analyses for the identification of normal cells (e.g. normal precursor B-cells, normal B-lymphocytes and normal plasma cells) and the comparison of the cell populations in samples from patients suspected to have PID with the cell populations in samples from healthy controls. For this purpose, a powerful multivariate analysis was used to assess the contribution of each individual marker in the panel to all other markers in the combination for separating the leukocyte populations. This strategy was used to select combinations of the most discriminating markers in multiple sequential rounds of experimental testing. Because of these multiple rounds of testing on samples of healthy controls and samples of well-defined PID patients, the final proposed antibody combinations became extremely strong when used in combination with the principal component analysis or canonical analysis, specifically with the automated population separation (APS) tool of the Infinicyt software, so that the added (independent) value of each marker is used in a single step of analysis.

The experimental section below provides representative examples of results from the extensive experimental studies for application of the EuroFlow PID Screening tube (Example 1), the EuroFlow PID pre-GC B-cell tube (Example 2), the EuroFlow PID Ig-Isotype B-cell tube (Example 3), and the EuroFlow T-cell subset tube (Example 4).

The Examples below demonstrate the power of the EuroFlow tubes according to the invention when analysed e.g. with principal component analysis, specifically with the APS tool. Based on multiple rounds of testing, the final antibody combinations appeared to be able to separate the different leukocyte, lymphocyte, B-cell subsets and T-cell subsets (FIG. 3, FIG. 4 and FIG. 6). Based on the fully standardized approach, the patterns of leukocyte and lymphocyte subsets of different healthy controls is fully comparable among different centers (FIG. 2, FIG. 4 and FIG. 6). The results from healthy controls have provided unique templates for the screening and classification of PID patients by plotting the results from PID patients against the templates obtained from healthy controls (see FIG. 3, FIG. 5 and FIG. 6).

Importantly, the PID tubes as analysed with the APS software tools are designed to provide templates of related leukocyte populations. This is particularly visible for the various B-cell and T-cell subsets, which show close relationships as in maturation pathways (FIG. 2 and FIG. 3). Plotting the results of patient samples against the APS templates of healthy controls easily visualizes altered distribution of leukocyte and lymphocyte subsets in PID patients. In fact, FIG. 3, FIG. 5 and FIG. 6 elegantly show which subsets are absent or (strongly) reduced in PID patients and what maturation block is present in particular patients, dependent on the type of defect.

The proposed 8-color, 10-color and 12-color tubes (Table 1, Table 2, and Table 3) provided herein are not only applicable for diagnosis and classification of PID patients. They are also perfectly suited for immune monitoring of patients with infections, autoimmune disease, allergy, post-transplantation, vaccination or other type of immune therapy, including antibody therapy. In contrast to other immunophenotyping approaches, the reagents and methods provided in the present invention both a more in-depth and a more integrated approach with powerful visualization of altered distribution between patients and controls as well as within patients over time during monitoring of disease course and recovery processes.

EXAMPLES

Example 1. EuroFlow PID Screening Antibody Panel

The screening tubes may be used to detect alterations of leukocytes subsets production associated with primary lymphoid tissues defects (BM and Thymus) such as STAT3, IL2RG and RAG2 defects (FIG. 3), although other defects related with the response in secondary lymphoid tissues might be also detected (e.g CD40L defects). Another example of application might be outcome monitoring after hematopoietic stem cell transplantation. These tubes can be used alone or in combination with B-cell tubes and/or T-cell tubes for a more detailed description of these subsets whenever is required, e.g. for immune monitoring.

The EuroFlow PID Screening Tube was tested on 20 blood samples from 15 healthy children and 5 children with recurrent infections. Based on preliminary reference values, established for the 15 healthy children, the 5 patients showed altered lymphocyte numbers in blood, with of different profiles: 1) Altered distribution of naïve/memory B-cells and T-cells was found in a patient with increased serum IgE who was later confirmed to have a STAT3 defect: 2) decreased T and NK-cell numbers with normal B-lymphocyte counts were found in two patients confirmed to have a mutation in the IL2RG gene; and 3) the remaining 2 cases showed significantly decreased numbers of B and T lymphocytes in blood, which were further demonstrated to be associated with a RAG2 gene defect. Examples of these patients are illustrated in FIG. 3.

Example 2. EuroFlow B-Cell Tubes

Among other applications, these tubes can be used for the detection of maturation blockades in the bone marrow (e.g. agammaglobulinemia: FIG. 5), defects on the B-cell response in the lymph nodes and/or other lymphoid tissues (e.g. CVID; FIG. 5) and isotype-specific defects (e.g. selective IgA deficiency; FIG. 6). These tubes might also be used for the monitoring of induced secondary immunodeficiencies such as induce by antibody therapies in hemato-oncology.

Ten bone marrow samples (5 normal bone marrow samples from 5 different healthy donors and 5 bone marrow samples from 5 different patients suffering from infection, who showed significantly decreased B-cell numbers after staining of a blood sample with the EuroFlow Screening tube) were stained with the EuroFlow B-cell tubes. For this purpose a lyse-stain-and-then-lyse/fix sample preparation technique was used, consisting of sequentially applying the EuroFlow bulk lysis method, followed by antibody staining for 30 minutes at room temperature, and final lyse-fixation with 10 mL, of the FACSLyse solution (Becton Dickinson Biosciences, San José, Calif., USA) diluted 1/10 (vol/vol) in distilled water for 10 minutes at room temperature. A complete B-cell maturation blockade at the early stages of maturation was found in 3 cases, two of which corresponded to agammablobulinemia patients with a BTK gene defect, while the third child was under treatment with the Rituximab anti-CD20 monoclonal antibody). In the other two patients normal bone marrow production of B-cells in the absence of plasma cells and significantly decreased numbers of switched IgA+ and IgG+ memory B-cells, both patients finally being diagnosed of CVID.

Example 3. Ig-Isotype B-Cell Tubes for Analysis of Healthy Donors and CVID Patients The EuroFlow Ig-Isotype tubes have been tested on blood samples from 10 healthy adults, 5 selective IgA-deficient individuals and 5 CVID patients (FIG. 6). Preliminary references values have been calculated for the distribution for IgM$^+$D$^{-/+}$, IgG1$^+$, IgG2$^+$, IgG3$^+$, IgG4$^+$, IgA1$^+$, IgA2$^+$, IgM$^-$D$^+$ memory B-cells (8-55, 21-33, 4-20, 3-10, <0.01-2, 8-25, 2-11, and <0.01-2 cells/μL) and plasmablasts/plasma cells (0.5-4.6, 0.3-1.0, 0.2-1.2, <0.01-0.2, <0.01-0.3, 0.4-3.8, 0.4-0.9, and <0.01-0.1 cells/μL). Evaluation of the same antibody combinations in the CVID patients has shown that, although lack of circulating plasmablasts/plasma cells (<0.01) seems to be a common feature to all patients investigated, Ig-isotype-expressing subsets of B-cells within the memory B-cell compartment are affected differently among different patients, suggesting that the state of the memory B-cell compartment might be directly associated with the level of immunocompetence to different antigens in these patients. Comparable alterations have been observed for individuals with selective IgA deficiency, but restricted to the IgA1 and IgA2 compartments of memory B-cells and plasmablasts/plasma cells.

Example 4. T-Cell Antibody Panels

The T-cell antibody panels are composed of sets of antibodies which aim at a more detailed description of T-cell subsets including the identification of central vs. effector memory B-cells, identification of terminally differentiated T-cells, and quantification of recent thymic emigrants (RTE) CD4$^+$ T-cells. These panels are specially recommended for the diagnostic classification of SCID patients, but they are also of interest for the identification of other alterations related with T-cell production (e.g. Di George syndrome).

A total of 5 blood samples from newborns presenting with facila alterations, heart disease and hypocalcemia were studied with the EuroFlow T-cell antibody panel using conventional multicolor direct immunofluorescence approaches using TrueCOUNT tubes; immediately after staining, the stained blood samples were measured in a FACSCANTO II flow cytometer (Becton/Dickinson Biosciences. San José Calif., USA). Two cases showed normal T-cell counts, and a normal distribution of the distinct T-cell subsets, while in the other three cases, decreased T-cell counts, particularly, decreased CD4+ T-cell counts (below 400 CD4+ T-cell per microliter of blood), were detected; in addition all three cases showed very low numbers of CD31+ CD4+ T-cells (recent thymic emigrants), suggesting a decreased T-cell production in the thymus. All 3 cases were shown to have a genetic deletion at chromosome 22q11.2, compatible with the diagnosis of Di George syndrome.

REFERENCES

Al Herz W, Aziz Bousfiha A, Casanova J L, Chatila T, Conley M E, Cunningham-Rundles C, Etzioni A, Franco J L, Gaspar H B, Holland S, Klein C, Nonoyama S, Ochs H, Oksenhendler E, Picard C, Puck J, Sullivan K, Tang M. Primary Immunodeficiency Diseases: An Update on the Classification from the International Union of Immunological Societies Expert Committee for Primary Immunodeficiency. Front Immunol 2014; 5:162

Biancotto A, Fuchs J C, Williams A, Dagur P K, McCoy J P Jr. High dimensional flow cytometry for comprehensive leukocyte immunophenotyping (CLIP) in translational research. J Immunol Meth 2011; 363:245-61.

Boldt A, Borte S, Fricke S, Kentouche K, Emmrich F, Borte M, Kahlenberg F, Sack U. Eight-color immunophenotyping of T-, B-, and NK-cell subpopulations for characterization of chronic immunodeficiencies. Cytometry B Clin Cytom 2014; 86: 191-206.

Duffy D, Rouilly V, Libri V, Hasan M, Beitz B, David M, Urrutia A, Bisiaux A, Labrie S T, Dubois A, Boneca I G, Delval C, Thomas S, Rogge L, Schmolz M, Quintana-Murci L, Albert M L; Milieu Intérieur Consortium. Functional analysis via standardized whole-blood stimulation systems defines the boundaries of a healthy immune response to complex stimuli. Immunity. 2014; 40:436-50.

Kalina T, Flores-Montero J, van der Velden V H, Martin-Ayuso M, Böttcher S, Ritgen M, Almeida J, Lhermitte L, Asnafi V, Mendonça A, de Tute R, Cullen M, Sedek L, Vidriales M B, Pérez J J, te Marvelde J G, Mejstrikova E, Hrusak O, Szczepański T, van Dongen J J, Orfao A; EuroFlow Consortium (EU-FP6, LSHB-CT-2006-018708). EuroFlow standardization of flow cytometer instrument settings and immunophenotyping protocols. Leukemia 2012; 26: 1986-2010.

Maecker H T, McCoy J P, Nussenblatt R. Standardizing immunophenotyping for the Human Immunology Project_Nature Reviews 2012; 12: 191-200.

Mishra A, Gupta M, Dalvi A, Ghosh K, Madkaikar M. Rapid Flow cytometric prenatal diagnosis of primary immunodeficiency (PID) disorders. J Clin Immunol 2014; 34: 316-322.

O'Gorman M R, Zollett J, Bensen N. Flow cytometry assays in primary immunodeficiency diseases. Methods Mol Biol 2011; 699: 317-335.

Oliveira J B, Notarangelo L D, Fleisher T A. Applications of flow cytometry for the study of primary immune deficiencies. Curr Opin Allergy Clin Immunol 2008; 8: 499-509.

Orfao de Matos Correia e Vale J A, Pedreira C E, Sobral Da Costa E. Method for generating new flow cytometry data files containing an infinite number of dimensions based on data estimation. U.S. Pat. No. 7,321,843 B2, 30 Sep. 2005

Orfao de Matos Correia e Vale J A, Pedreira C E, Sobral Da Costa E. Multidimensional detection of aberrant phenotypes in neoplastic cells to be used to monitor minimal disease levels using flow cytometry measurements. U.S. Pat. No. 7,507,548 B2, 4 Mar. 2003

Streitz M, Miloud T, Kapinsky M, Reed M R, Magari R, Geissler E K, Hutchinson J A, Vogt K, Schlickeiser S, Kverneland A H, Meisel C, Volk H D, Sawitzki B. Standardization of whole blood immune phenotype monitoring for clinical trials: panels and methods from the ONE study. Transplant Res 2013; 2: 17.

Van Dongen J J M, Orfao de Matos Correia e Vale J A, Flores-Montero J, Almeida P J M, Van der Velden V H J. Böttcher S, Rawstron A C, De Tute R M, Lhermitte L B S, Asnafi V, Mejstríková E, Szczepanski T, Da Silva Lucio P J M, Marín Ayuso M, Pedreira C E. Methods, reagents and kits for flow cytometric immunophenotyping. WO2010140885 A1, 3 Jun. 2009.

Van Dongen J J, Lhermitte L, Böttcher S, Almeida J, van der Velden V H, Flores-Montero J, Rawstron A, Asnafi V, Lécrevisse Q, Lucio P, Mejstrikova E, Szczepański T, Kalina T, de Tute R, Brüggemann M, Sedek L, Cullen M, Langerak A W, Mendonça A, Macintyre E, Martin-Ayuso M, Hrusak O, Vidriales M B, Orfao A; EuroFlow Consortium (EU-FP6, LSHB-CT-2006-018708). EuroFlow antibody panels for standardized n-dimensional flow cytometric immunophenotyping of normal, reactive and malignant leukocytes. Leukemia 2012; 26:1908-1975.

The invention claimed is:

1. A reagent composition for the flow cytometric immunophenotyping of leukocytes comprising fluorochrome-conjugated antibodies directed against the following combination of markers:

CD27, IgM, IgG3, IgG2, IgG1, IgD, CD19, CD21, and CD38; the reagent composition comprising two distinctly labeled antibodies against IgG2; wherein the first antibody against IgG2 and the antibody against IgG3 are each conjugated to a first fluorochrome, and wherein the second antibody against IgG2 and the antibody against IgG1 are each conjugated to a second fluorochrome; and wherein the first and the second fluorochromes are distinguishable.

2. The reagent composition according to claim 1, further comprising fluorochrome-conjugated antibodies against IgA1, IgA2 and IgG4, the composition comprising two distinctly labeled antibodies against IgA1; wherein the first antibody against IgA1 and the antibody against IgG4 are each conjugated to a third fluorochrome, and wherein the second antibody against IgA1 and the antibody against IgG4 are each conjugated to a fourth fluorochrome; and wherein the third and the fourth fluorochromes are distinguishable.

3. The reagent composition according to claim 2, further comprising fluorochrome-conjugated antibodies against CD5 and CD24.

4. The reagent composition or set of reagent compositions according to claim 1, wherein each reagent composition comprises antibodies conjugated to (1) pacific blue (PacB), brilliant violet 421 (BV421) or Horizon V450; (2) pacific orange (PacO), Horizon V500 (HV500), BV510, Khrome orange (KO) or OC515, (3) Horizon BB515, fluorescein isothiocyanate (FITC) or Alexa488, (4) phycoerythrin (PE), (5) peridinin chlorophyl protein/cyanine 5.5 (PerCP-Cy5.5), PerCP or PE-TexasRed, (6) phycoerythrin/cyanine7 (PE-Cy7), (7) allophycocyanine (APC) or Alexa647, and (8) allophycocyanine/hilite 7 (APC-H7), APC-Cy7, Alexa680, APC-A750, APC-C750 or Alexa700.

5. The reagent composition or set of reagent compositions according to claim 4, wherein each reagent composition comprises antibodies conjugated to (1) brilliant violet 421, (2) brilliant violet 510 (BV510), (3) brilliant violet 650 (BV650), (4) brilliant violet 786 (BV786), (5) fluorescein isothiocyanate (FITC), (6) peridinin chlorophyl protein/cyanine 5.5 (PerCP-Cy5.5), (7) to phycoerythrin (PE), (8) phycoerythrin/cyanine7 (PE-Cy7), (9) allophycocyanine (APC), and (10) allophycocyanine/H7 (APC-H7), APC-C750 or APC-Alexa750.

6. A kit comprising:
(i) the reagent composition of claim 1; and
(ii) a second reagent composition comprising the following combination of markers:
CD27, IgM, IgA2, IgA1, IgG4, IgD, CD19, CD21, and CD38; the second reagent composition comprising two distinctly labeled antibodies against IgA1; wherein the first antibody against IgA1 and the antibody against IgG4 are each conjugated to a third fluorochrome, and wherein the second antibody against IgA1 and the antibody against IgA2 are each conjugated to a fourth fluorochrome; and wherein the third and the fourth fluorochromes are distinguishable.

7. A kit comprising:
(i) the reagent composition of claim 1;
(ii) a second reagent composition comprising the following combination of markers:
CD27, IgM, IgA2, IgA1, IgG4, IgD, CD19, CD21, and CD38; the second reagent composition comprising two distinctly labeled antibodies against IgA1; wherein the first antibody against IgA1 and the antibody against IgG4 are each conjugated to a third fluorochrome, and wherein the second antibody against IgA1 and the antibody against IgA2 are each conjugated to a fourth fluorochrome; and wherein the third and the fourth fluorochromes are distinguishable; and
(iii) a third reagent composition comprising the following combination of markers:
CD27, CD45RA, CD8, IgD, CD16, CD56, CD4, IgM, CD19, CD3, CD45, and either TCRαβ or TCRγδ, wherein the antibody against CD8 and the antibody against IgD are each conjugated to a fifth fluorochrome, and wherein the antibody against CD16 and the antibody against CD56 are each conjugated to a sixth fluorochrome, and wherein the antibody against CD4 and the antibody against IgM are conjugated to a seventh fluorochrome, and wherein the antibody against CD19 and the antibody against TCRαβ or TCRγδ are each conjugated to an eighth fluorochrome; and wherein the fifth, sixth, seventh, and eighth fluorochromes are distinguishable.

* * * * *

UNITED STATES PATENT AND TRADEMARK OFFICE
CERTIFICATE OF CORRECTION

PATENT NO. : 10,802,023 B2
APPLICATION NO. : 15/523309
DATED : October 13, 2020
INVENTOR(S) : Jacobus Johannes Maria Van Dongen et al.

It is certified that error appears in the above-identified patent and that said Letters Patent is hereby corrected as shown below:

In the Claims

Column 19, Line 52, please delete "or set of reagent compositions"

Column 20, Line 6, please delete "or set of reagent compositions"

Signed and Sealed this
Ninth Day of March, 2021

Drew Hirshfeld
*Performing the Functions and Duties of the*
*Under Secretary of Commerce for Intellectual Property and*
*Director of the United States Patent and Trademark Office*